United States Patent [19]
Bischof et al.

[11] 4,204,963
[45] May 27, 1980

[54] SEALING MEMBERS FOR A MEMBRANE DIFFUSION DEVICE

[75] Inventors: Daniel F. Bischof, McHenry; John M. Munsch, Libertyville, both of Ill.

[73] Assignee: Baxter Travenol Laboratories, Inc., Deerfield, Ill.

[21] Appl. No.: 926,466

[22] Filed: Jul. 20, 1978

[51] Int. Cl.² ............................................. B01D 31/00
[52] U.S. Cl. ................... 210/321 B; 210/350; 210/450; 422/48
[58] Field of Search ............... 210/321 B, 321 A, 351, 210/224, 227, 350, 450, 455, 493 M, 493 R, 493 B; 422/48; 100/211; 55/158; 114/54; 9/2 A, 13; 206/522; 277/115; D23/47; 49/477

[56] References Cited
U.S. PATENT DOCUMENTS

| | | | |
|---|---|---|---|
| 3,199,689 | 8/1965 | Feldkamp | 206/522 |
| 3,522,885 | 8/1970 | Lavender et al. | 210/321 R |
| 3,743,097 | 7/1973 | Sausse | 210/321 B |
| 3,879,293 | 4/1975 | Wolf, Jr. et al. | 210/321 B |
| 3,907,687 | 9/1975 | Hoeltzenbein | 210/321 B |
| 4,028,252 | 6/1977 | Morris | 210/321 B |
| 4,133,764 | 1/1979 | Bardin et al. | 210/236 |

Primary Examiner—Charles N. Hart
Assistant Examiner—David R. Sadowski
Attorney, Agent, or Firm—Paul C. Flattery; Garrettson Ellis

[57] ABSTRACT

Improvements are provided in the sealing arrangment and in an inflatable shim for a membrane diffusion device which comprises a stack of membrane sections and means for defining interleaving flow paths for two different fluids, separated by the membranes.

7 Claims, 5 Drawing Figures

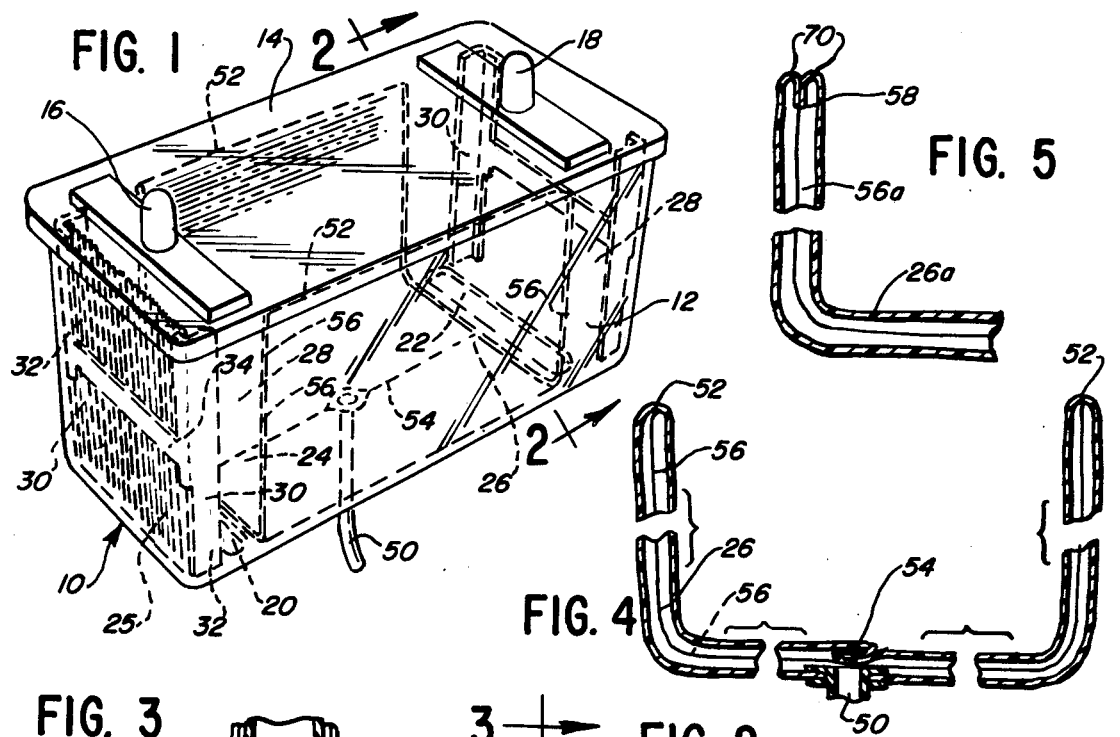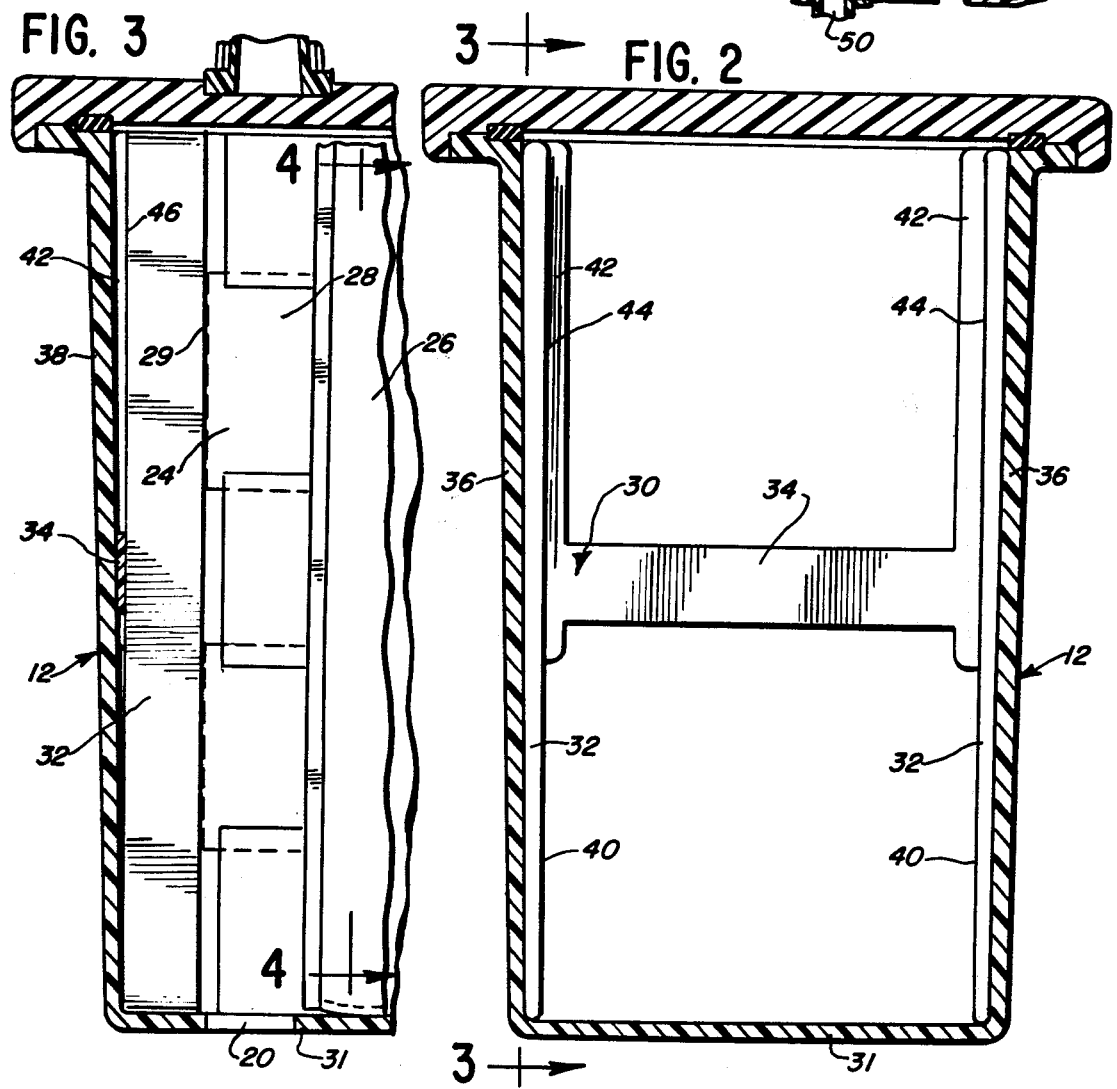

SEALING MEMBERS FOR A MEMBRANE DIFFUSION DEVICE

BACKGROUND OF THE INVENTION

In U.S. Pat. No. 3,879,293 a membrane diffusion device is disclosed having an inflatable member for pressurization and sealing. The inflatable member is U-shaped, to be positioned about the major faces and the bottom side of a stack of membrane sections separated by membrane support member means, and defining interleaving flow paths for two different fluids, separated by the membranes.

The purpose of an inflatable member, whether a flat member as is well known in the prior art, or the U-shaped member of the above patent, is to selectively apply pressure to the membrane stack by inflation while the stack is retained in a rigid casing, to prevent undue spreading of the fluid paths in the stack when pressurized fluid is provided. This is particularly important in the case where the device is intended for use as a blood oxygenator, an artificial kidney, or the like.

The invention of this application provides means for increasing the relative amount of surface area of the stack which is subjected to the effect of the inflatable shim. Also, a novel improvement in the end seal for the stack is provided, to further reduce the possibility of leakage from the ends of the membrane stack.

DESCRIPTION OF THE INVENTION

In accordance with this invention, a membrane diffusion device is provided which comprises a stack of flat membrane wall pairs and flat membrane supports in alternating, interleaving relation, the stack being disposed in a casing and defining opposed ends. The casing walls in turn define a small draft angle, generally as an inevitable consequence of economical molding processes, while the stack itself generally has parallel, opposed sides.

In accordance with this invention, there is positioned about each end of the stack a rigid shim member spaced at the outer corners of said stack, between said stack and the angularly oriented inner walls of the casing, said rigid shim member being correspondingly tapered at an angle corresponding to the draft angle of the inner wall of the casing, and proportioned to compress the end portions of the stack to a degree which is generally equal across the entire length of the rigid shim members.

Preferably, the shim member fits about each outer corner of the stack and defines correspondingly tapered elements in compressing contact with both the sides and ends of the stack adjacent each corner, for compressing action in two directions against the stack.

The effect of this is to center the stack in the casing, and to constantly and uniformly compress its ends in a manner which eliminates the non-uniformity of compression of the stack, which may take place when the membrane stack is inserted in a casing having walls that are slightly non-parallel. This helps to reinforce the end seal of the membrane stack, which may be a potted seal, for example as described in U.S. Pat. No. 3,757,955, putting a constant compression upon the potted seal elements to prevent seal failure. Also, the rigid shim members make the stack ends rigid which reduces the possibility of peel stress at the stack ends on the end seals due to fluctuating pressures.

It is further desirable for each of the rigid, tapered shim members at respective ends of the stack to be connected together by a crossbar member to form an integral H-shaped unit for ease of assembly, and for further support of the ends of the stack against the casing.

Further in accordance with this invention, an improvement in the inflatable shim member of this invention is disclosed. As previously described in U.S. Pat. No. 3,879,293, the ends of an inflatable member, upon being inflated, naturally tend to retract. This, in turn, tends to expose some of the membrane stack so that it is not acted upon by the inflated shim member.

When the inflatable member is made of a pair of heat-sealed sheets in conventional manner, a flat, peripheral heat seal exists around the edge. This means that the shim must be further shortened in order to permit the casing to be effectively sealed adjacent the shim ends without interference by the peripheral heat seal. This serves to increase the problem of withdrawal of the inflated shim.

In accordance with this invention, an inflatable member is provided, being made of a double-folded, flexible member having a central seal line, spaced from the edges of the flexible member except at the ends of the seal line, with the two opposed folded ends of the resulting inflatable, sealed member comprising seal-free opposed ends. These ends, being free of a heat sealed flange, may, in the original assembly of the diffusion device, abut closely against the casing, so that as they inflate their withdrawal is less, compared with inflatable members used for pressurizing a membrane stack as in the prior art.

As an alternative embodiment, the inflatable member may exhibit ends in which the sealed flange holding the two sides of the inflatable member together is positioned inwardly from the outer end of the inflatable member, with a pair of adjacently-positioned, folded membrane walls defining the outer end, and the heat seal being positioned within the inflatable chamber of the flexible, inflatable member. This structure also permits the same significant increase in the area of the membrane stack which is pressurized by the inflatable membrane.

Referring to the drawings,

FIG. 1 is a perspective view of an oxygenator for blood, utilizing the invention of this application, with certain internal parts being shown in phantom lines.

FIG. 2 is a vertical sectional view of an end of the blood oxygenator of Claim 1, taken along line 2—2 of FIG. 1.

FIG. 3 is a fragmentary sectional view of an end of the blood oxygenator taken along 3—3 of FIG. 2.

FIG. 4 is an isolated sectional view, greatly magnified and with sections broken out, of the inflatable member utilized in FIGS. 1 through 3, taken along line 4—4 of FIG. 3.

FIG. 5 is a fragmentary sectional view similar to that of FIG. 4, showing a portion of a second embodiment of the inflatable member of this invention.

Referring to FIGS. 1 through 4, the membrane oxygenator for blood which is illustrated is similar to that shown in U.S. Pat. No. 3,879,293, but having the improvements as described herein.

Oxygenator 10 defines a casing 12 which is closed with a top member 14, and includes a sealed inlet port 16 and outlet port 18 for blood.

Apertures 20, 22 on the under side of casing 12 are for connection with an oxygen inlet and outlet conduit, respectively, with the flow of oxygen usually being in counter-current relation to the flow of blood. Specifically, oxygenator 10 is adapted for use with apparatus described in U.S. Pat. No. 4,061,470 for the oxygenation of the blood of a patient undergoing heart surgery or the like.

A convoluted membrane stack 24 is provided as described in the previously cited patents and particularly, U.S. Pat. No. 3,757,955, being adapted for flow communication in separate, multiple interleaving flow paths with blood inlet and outlet 16, 18 and oxygen inlet and outlet 20, 22. Positioned about the central portion of stack 24 is the U-shaped, inflatable member 26 for pressurizing the central portions of the stack 24. Positioned adjacent the outer edges of inflatable member 26 are the longitudinally extending cut-away portions 28 of the folded membrane support backing 29, which serve as a manifolding means for distributing the blood and the oxygen in their respective flow paths throughout the convoluted area of the membrane, for uniform flow across the great majority of the membranes in stack 24. The ends 25 of stack 24 are sealed with a potting compound, for example, as described in the previously cited patent, to prevent leakage from the respective flow paths out of the ends of the membrane stack 24. Cover 14 is correspondingly sealed to casing 12.

In accordance with this invention, rigid shim member means 30, positioned in the respective ends of casing 12, provides a constant compressive pressure against the ends of stack 24 to reinforce the sealing capabilities of the potted ends. As shown, each shim member means 30 comprises a pair of tapered, rigid upstanding members 32, connected together by a cross member 34 to define a generally H-shaped structure, which may be made out of polyethylene, polystyrene, or the like by a simple and inexpensive molding operation. The potted ends of stack 24 are positioned between tapered members 32 at each end of casing 12. Tapered members 32 and stack 24 are so proportioned that the ends of the stack are compressed between tapered members 32 which in turn abut against the inner wall of casing 12, to reinforce the sealing capabilities of the potted ends of the stack.

As shown in FIGS. 2 and 3, side walls 36 and end walls 38 of container 12 define inner surfaces which are not parallel to each other but diverge slightly outwardly from the bottom wall 31. The reason for this is that there are very important economic advantages in the available molding processes for casing 12 to design casing 12 with a slight (for example 1°) outward taper or angle of draft, to facilitate removal of the core from the casing after the molding operation is complete.

In accordance with this invention, tapered members 32 correspondingly define an increased thickness from the bottom to the top, as shown in FIG. 2, corresponding to the draft angle of the inner surfaces of walls 36, so that the inner surfaces 40 of tapered members are generally parallel, the outer surfaces thereof diverging in a manner corresponding to the draft angle of the housing 12.

Each of tapered members 32 also define an end flange member 42, which serves to retain the ends of stack 24 in precisely positioned relationship, with the corners of stack 24 fitting in corners 44 defined between each tapered member 32 and flange 42.

As shown in FIG. 3, the inner surfaces of end walls 38 of casing 12 also exhibit an outward draft angle, and each flange 42 is correspondingly tapered so that their inner surfaces 46 are parallel to each other, while their outer surfaces also diverge in a manner corresponding to the draft angle of walls 38.

As a result of this, the H-shaped, rigid shim members 30 may be positioned about the corners of membrane stack 24 and placed into casing 12, providing a generally constant lateral compression against the ends of stack 12 at the great majority of vertical positions thereof, despite the fact that the walls of casing 12 diverge in a small draft angle. As a result of this, especially at the upper portions of the ends of stack 12, each shaped, rigid shim member 30 provides an essentially equal amount of compression to that which is sensed by the lower portions of the ends of stack, due to the tapering configuration of the upstanding members 32. This eliminates the otherwise variable effect of the tapered walls of casing 12. The effect of this is to provide further insurance against leakage of fluid taking place through the sealed ends of stack 24.

FIG. 4 illustrates structural details of U-shaped inflatable member 26. Inflatable member 26 may be overall similar in shape and function to the corresponding U-shaped inflatable member of U.S. Pat. No. 3,879,293, being a flexible, inflatable structure which may be held in a U-shape about three sides of stack 24, and which contains an inflation port and line 50.

At the ends of the member where a flat, periphal heat seal existed in the prior art, only a folded end 52 is found in the embodiment of FIG. 4. The entire inflatable member 26 comprises a single sheet, which is double folded at ends 52 and heat sealed along line 54, which is parallel to the lines of ends 52. Heat seal 54 may be spaced from the edges of flexible, inflatable member 26, except, of course, at its ends, lapping two layers of the inflatable member over in the manner shown to create a single cross-sectional loop.

The respective opposed sides 56 between ends 52 of inflatable member 26 may then be sealed together with a transverse bar seal or the like, for sealing member 26.

Member 26 is then wrapped around stack 24, to be placed into the U-shaped configuration, as shim members 30 are placed on the ends of the stack. Then the entire assembly may be placed into casing 12 for assembly of the device of this invention.

FIG. 5 shows an alternative embodiment 26a of the inflatable, U-shaped member of this invention, being of essentially similar construction to the embodiment of FIG. 4 except as shown herein. In this instance, member 26a may comprise a pair of peripherally heat sealed sheets made of polyvinyl chloride as in previous embodiments. However, heat-sealed flange 58 holds the two sides of the inflatable member 26a together, and is positioned inwardly from the outer end of the inflatable member 26a, which outer end is defined by a pair of adjacently-positioned, folded membrane walls 70, with heat seal 58 being inwardly positioned and folded within the inflatable chamber of the flexible, inflatable member 26a. The opposite end of inflatable member 26a may be of similar construction, while the adjacent sides may be sealed with a bar seal line 56a as in the previous embodiment.

The resulting oxygenator can exhibit the remarkable advantages of this type of oxygenator, particularly when porous hydrophobic membrane is used, for example, polypropylene film having a pore size of 0.1 micron, having remarkably improved gas transfer rates. At the same time, this invention provides added insurance against leakage which may take place due to the oscillating blood pressures in the oxygenator, and also provides a substantial improvement in the overall oxygen and carbon dioxide transfer rates.

In the specific embodiment, the width of the chamber of casing 12 at its bottom, adjacent to wall 31, as shown in FIG. 2, may be about 3.1 inches. The corresponding width of the top of the casing may be about 3.2 inches, to provide a 0.1 inch draft in the casing. The tapering of member 30 corresponds to this.

The above has been offered for illustrative purposes only, and is not intended to limit the invention of this application, which is as described in the claims below.

That which is claimed is:

1. A membrane diffusion device which comprises a stack of membrane wall pairs and membrane supports in alternating, interleaving relation, the stack being disposed in a casing and defining opposed ends, the casing inner walls defining a draft angle, the improvement comprising:

rigid shim member means spaced at the outer corners of said stack between said stack and the inner walls of the casing, said rigid shim member means being tapered and proportioned to compress the end portions of said stack between said inner walls of the casing and said shim member means to a degree which is generally equal across the entire length of said rigid shim member means, the rigid, tapered shim member means at respective ends of the stack being connected together by a cross bar member to form an integral unit.

2. The membrane diffusion device of claim 1 which said shim member means fit about each outer corner of the stack and define correspondingly tapered elements in compressing contact with both the sides and the ends of the stack adjacent each corner, for compressing and positioning action in two directions against the stack.

3. The membrane diffusion device of claim 2 in which the opposed sides of said stack are generally parallel to each other.

4. The membrane diffusion device of claim 3 which includes an inflatable member positioned adjacent said stack, said inflatable member comprising a double-folded, flexible member defining a central seal line spaced from the edges of the flexible member except at the end thereof, and defining two opposed, folded ends which are free of seal lines, said ends being positioned closely against the casing between the sides of the stack and the walls of said casing, whereby, upon inflation, the degree of withdrawal of said seal lines is less compared with inflatable members which carry a seal line on their ends.

5. The membrane diffusion device of claim 3 in which an inflatable member is positioned adjacent the stack between the sides of the stack and the walls of said casing, said inflatable member defining opposed ends, and a seal line defining a flange carried adjacent said opposed ends, said opposed ends being defined by a pair of adjacently-positioned, folded membrane walls, said flange being positioned within the inflatable chamber of said flexible member at a position spaced toward the center of said inflatable member from the opposed ends, said opposed ends being positioned closely against said casing, whereby upon inflation withdrawal is less compared with inflatable members which define an outwardly-projecting flange seal at their opposed ends.

6. A membrane diffusion device which comprises a stack of membrane wall pairs and membrane supports in alternating, interleaving relation, said stack being disposed in a casing having a lid, and an inflatable member positioned adjacent said stack, said inflatable member comprising a double-folded, flexible member defining a central seal line spaced from the edges of the flexible member except at the ends thereof, and defining two opposed, folded ends which are free of seal lines, said ends being positioned closely adjacent the casing and between said stack and casing adjacent said lid whereby, upon inflation, the degree of withdrawal of said seal lines is less compared with inflatable members which carry a seal line.

7. A membrane diffusion device which comprises a stack of membrane wall pairs and membrane supports in alternating, interleaving relation, said stack being disposed in a casing having a lid, and an inflatable member positioned adjacent said stack, said inflatable member defining opposed ends positioned between said stack and casing, and a seal line defining a flange carried adjacent said opposed ends, said opposed ends being defined by a pair of adjacently positioned, folded membrane walls, said flange being positioned within the inflatable chamber of said flexible member at a position spaced toward the center of said inflatable member from the opposed ends, said opposed ends being positioned closely against said casing adjacent said lid, whereby upon inflation their withdrawal is less compared with inflatable members which define an outwardly projecting flange seal at their opposed ends.

* * * * *